United States Patent [19]

Makino et al.

[11] Patent Number: 4,985,244

[45] Date of Patent: Jan. 15, 1991

[54] STABILIZED LIVE ATTENUATED VACCINE AND ITS PRODUCTION

[75] Inventors: Satoshi Makino; Keiko Sasaki, both of Kanagawa; Masaharu Nakagawa, Tokyo, all of Japan

[73] Assignee: The Kitasato Institute, Tokyo, Japan

[21] Appl. No.: 203,411

[22] Filed: Jun. 8, 1988

[30] Foreign Application Priority Data

Jun. 8, 1987 [JP] Japan .................................. 62-142465

[51] Int. Cl.$^5$ ......................... A61K 39/12; C12N 7/00
[52] U.S. Cl. ...................................... 424/89; 435/235; 435/236; 435/238; 435/239
[58] Field of Search ................... 424/89; 435/235, 236, 435/238, 239

[56] References Cited

U.S. PATENT DOCUMENTS

| | | | |
|---|---|---|---|
| 4,337,242 | 6/1982 | Markus et al. | 424/89 |
| 4,338,335 | 7/1982 | McAleer et al. | 424/89 |
| 4,500,512 | 2/1985 | Barme . | |

FOREIGN PATENT DOCUMENTS

| | | |
|---|---|---|
| 67887/87 | 7/1987 | Australia . |
| 0028563 | 5/1981 | European Pat. Off. . |
| 2424031 | 11/1979 | France . |

OTHER PUBLICATIONS

"Stability on Storage at Various Temperatures of Live Measles, Mumps and Rubella Virus Vaccines in New Stabilizer", *Journal of Biological Standardization*, vol. 8, No. 4, 1980, by William McAleer et al., pp. 281–287.
"Behaviour of Five Commercial Measles Vaccines in an Accelerated Stability Test", *Journal of Biological Standardization*, vol. 10, No. 3, 1982, by G. Colinet et al., pp. 241–247.
"Thermodegradation of Lyophilized Measles Vaccines", *Reviews of Infectious Diseases*, vol. 5, No. 3, May–Jun., 1983, by F. E. Andre, pp. 532–534.
"Thermostability of Live Freeze-Dried Measles Vaccine After Reconstitution", *Proc. Symposium on Stability and Effectiveness of Measles, Poliomyelitis and Pertussis Vaccines*, by D. Ikic et al., pp. 103–112.
"The Influence of Storage at 37° C. on the Potency of Frezze-Dried and Reconstituted Live Measles Vaccine", *Proc. Symposium on Stability and Effectiveness of Measles, Poliomyelitis and Pertussis Vaccines*, by H. Cohen et al., pp. 95–101.
"10th International Immunobiological Symposium", *Proceedings, Symposium on Stability and Effectiveness of Measles, Poliomyelitis and Pertussis Vaccines*, Organized by Yugoslav Academy of Sciences and Arts and Institute of Immunology, Sep. 1976, pp. 87–94.

*Primary Examiner*—Howard E. Schain
*Assistant Examiner*—Abdel A. Mohamed
*Attorney, Agent, or Firm*—Young & Thompson

[57] ABSTRACT

A stabilized live attenuated vaccine with improved thermal stability, which comprises a live attenuated plain vaccine consisting of measles, mumps or rubella virus grown in a medium-199 for cell culture, or a combined live attenuated vaccine thereof, containing a stabilizing agent at a final concentration of lactose 2.5–5 W/V %, saccharose 2.5–5 W/V %, D-sorbitol 1.8–2 W/V %, sodium glutamate about 0.1 W/V % and gelatin hydrolyzate, M.W. approx. 35,000, 2–3 W/V %.

3 Claims, 2 Drawing Sheets

STABILIZED LIVE ATTENUATED VACCINE AND ITS PRODUCTION

FIELD OF THE INVENTION

This invention relates to a stabilized live attenuated vaccine and its production.

BACKGROUND OF THE INVENTION

Titers of live attenuated vaccines are usually thermally unstable. Vaccine preparations are therefore supplied as low-temperature frozen products or lyophilized products. To stabilize them, a chemical stabilizing agent is added to the vaccine solution. Examples of chemical stabilizing agents hitherto known are human albumin, gelatin hydrolyzate, sugar alcohols, amino acids and other non-toxic substances. For example, for this purpose it is known to use a preparation consisting of a basic amino acid such as arginine, lysine or histidine, each 5 W/V% or adding thereto various sugar alcohols such as saccharose, inositol or sorbitol, each 5 W/V% (Jap. Patent Appln. No. 45-1887), a preparation obtained by mixing peptone 5-10 W/V%, arginine or lysine 3 W/V% and saccharose 5 W/V% (Jap. Patent Unexam. Publ. No. 50.2225), a preparation obtained by adding lactose 4 W/V% and sorbitol 2 W/V% to a phosphate buffer solution containing $Ca^{++}$ and $Mg^{++}$, or adding at least one amino acid 0.005M-0.05M thereto (Jap. Patent Appln. No. 57-81338), a preparation consisting of lactose 5 W/V%, D-sorbitol 1.5 W/V%, dextran 70 0.3W/V%, potassium glutamate 0.048%, disodium phosphate 0.0625 W/V%, potassium phosphate 0.026 W/V%, gelatin 0.3 W/V% and human albumin 0.25 W/V% (Jap. Patent Appln. No. 55-80465), and a preparation wherein a vaccine solution is acidified to pH 6.0-6.5 prior to lyophilization by adding a phosphate buffer solution containing a stabilizing agent comprising a gelatin partial hydrolyzate, M.W. approx. 3,000, sorbitol, saccharose, lactose, maltose, L-glutamate and L-arginine (Jap. Patent Unexam. Publ. No. 57-114527).

Nowadays, vaccines are distributed to tropical countries where there are no refrigerated distribution sytems. In these areas, the vaccine preparations supplied must have heat stability at high temperature. The above known stabilizing agents were not suitable in this regard.

We have found that a live attenuated vaccine shows strong thermostability when lactose, D-sorbitol, saccharose, gelatin hydrolyzate and sodium glutamate at specific ratios of concentration are added to a vaccine virus suspension comprising a medium-199 for cell culture (Morgan, et al., Proc. Soc. Exp. Biol. Med , 73:1-8, 1950) (hereinafter designated as medium-199). Each component thereof has been known as a stabilizing agent for live attenuated vaccines; however, it has never been known that a combination thereof at a specific ratio of concentrations exhibits unexpected thermostability.

OBJECTS OF THE INVENTION

An object of the present invention is to provide a stabilized live attenuated vaccine comprising an admixture of a conventional live attenuated vaccine with lactose, D-sorbitol, saccharose, gelatin hydrolyzate and sodium glutamate at specific ratios of concentration.

Another object of the present invention is to provide a stabilized live attenuated vaccine which comprises a conventional live attenuated plain vaccine which is measles, mumps or rubella virus grown in a medium-199 for cell culture, or a combined live attenuated vaccine thereof, containing a stabilizing agent.

A further object of the present invention is to provide a process for preparing live attenuated vaccines.

SUMMARY OF THE INVENTION

In the present invention, a vaccine solution is prepared by growing a seed virus in a culture system using medium-199. Examples of live attenuated vaccine are plain or combined vaccines of measles, mumps or rubella. A thermostable high titer vaccine can be obtained by adding the additives recited below, at specific concentrations and lyophilizing the vaccine solution. A further specific feature of the present invention is that it is not required to adjust the pH of the vaccine solution below neutral pH but only to add each sterilized component prior to lyophilization. A still further advantage of the present invention is that it does not contain human albumin, which provides a superior stabilization effect, and so the present additives are safer chemical compounds. Therefore the adverse effect of an immunological preparation caused by its carrier or vehicle can be reduced.

The composition of the present stabilizing agent is illustrated as follows. The components and the final concentration of the stabilizing agent in the final bulk vaccine solution which is composed of an original cultured vaccine using a medium-199 and a diluent for medium-199, are lactose 2.5-5 W/V%, saccharose 2.5-5 W/V%, D-sorbitol 1.8-2 W/V%, sodium glutamate about 0.1 W/V% and gelatin hydrolyzate, M.W. approx. 35,000, 2-3 W/V%. These substances are dissolved in medium-199 at preferred concentrations and are aseptically filtered.

The thermostability of the vaccine of the present invention can be observed by virus suspension (Table 1), and is more apparently in the lyophilized product (Table 2). The thermostability of the lyophilized live attenuated vaccine product containing a stabilizing agent of the present invention is superior to that of the known vaccine preparations containing conventional stabilizing agents. For example, when a measles vaccine preparation containing a conventional stabilizing agent consisting of lactose 5 W/V%, sodium glutamate 0.1 W/V% and gelatin hydrolyzate 0.2 W/V% as its final concentration, is kept at 37° C. for one week, its titer decreases to 1/100-1/500 with corresponding loss of immunogenicity. On the contrary, a product containing a stabilizing agent of the present invention loses not more than one third of its titer under the same conditions and so retains its immunogenicity as compared with the titer of the original vaccine preparation.

As shown in FIGS. 1 and 2, the thermostability of mumps and rubella vaccines containing a stabilizing agent of the present invention is also superior to that of a commercial vaccine preparation containing conventional stabilizing agents. Live attenuated measles vaccine containing the stabilizing agent of the present invention can be used for the worldwide project for the eradication of measles sponsored by WHO, including the countries having no refrigerated distribution systems.

The following example illustrates the present invention but is not to be construed as limiting.

EXAMPLE

Lactose 5 W/V%, saccharose 5 W/V%, D-sorbitol 1.8 W/V%, sodium glutamate 0.1 W/V% and gelatin hydrolyzate, M.W. approx. 35,000, 2 W/V%, final concentration, (Behringwerke AG, West Germany, gelatin hydrolyzate powder dissolved in medium-199 "HEMA-CEL" (trade name: Gelatin hydrolyzate for liquid transfusion)) were added to a measles vaccine virus suspension in medium-199 to prepare a bulk vaccine (2 batches). The vaccine is lyophilized and finally five aliquots of vaccine preparation were produced. A comparative accelerated heat stability test with the product hereinabove and with a commercial lyophilized vaccine product (four aliquots) was performed.

Figure 1:
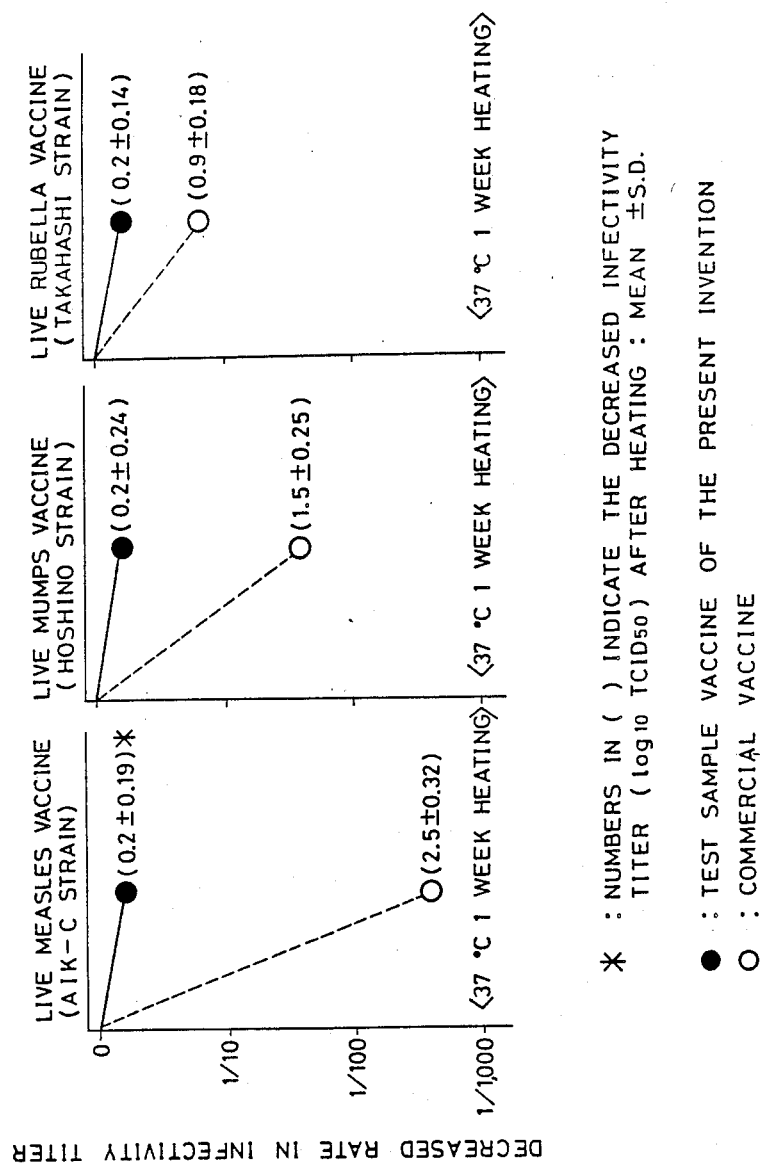
FIGS. 1 and 2 show the heat stability of vaccines containing a stabilizing agent of the present invention, and that of the commercially available vaccines.
Figure 2:
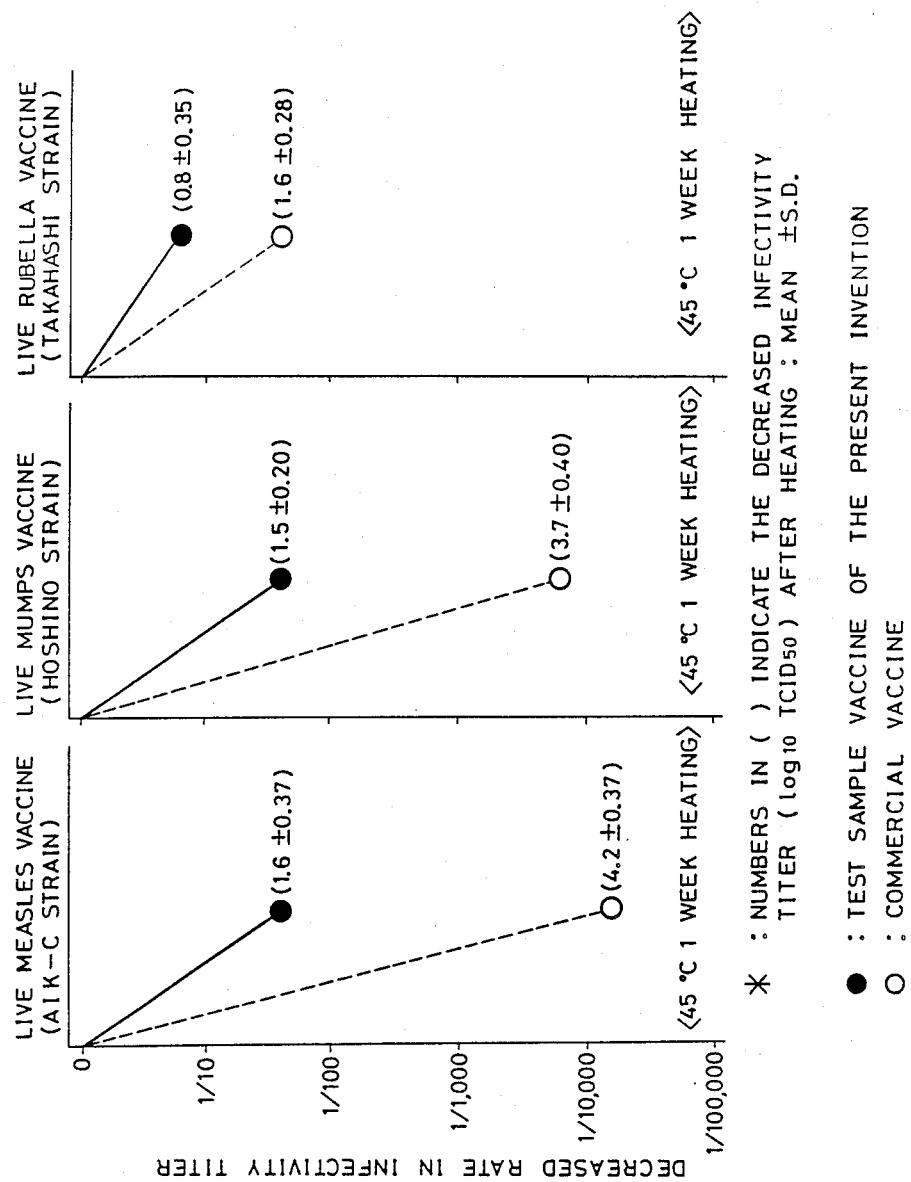

Also a live attenuated mumps or rubella vaccine containing the stabilizing agent of the present invention hereinabove was prepared, in two batches, and the vaccine solution was lyophilied to prepare four aliquots of the products. Comparative accelerated heat stability tests were run with the products hereinabove and with commercial lyophilized vaccine products (two aliquots each). As shown in Table 2 and FIGS. 1 and 2, the decrease in titer of the lyophilized live attenuated vaccine of measles, mumps and rubella containing a stabilizing agent of the present invention, after storage at 37° C. and at 45° C. for one week, respectively, is significantly less than that of the commercially available conventional vaccines.

TABLE 1

Survival ratio of vaccine virus in medium - 199 containing stabilizing agent of the present invention and in conventional liquid for vaccine, after heating at 37° C.

| suspension | vaccine virus | infectivity titer before heating * | Survival ratio of virus after heating at 37° C. ☆ | |
|---|---|---|---|---|
| | | | after 6 hrs. | after 18 hrs. |
| medium-199 containing stabilizing agent | measles (AIK-C strain) | 4.1 | 1.0% | ≦0.064% |
| conventional liquid for vaccine | measles (AIK-C strain) | 4.2 | 0.2% | ≦0.031% |
| medium-199 containing stabilizing agent | mumps (HOSHINO strain) | 4.4 | 5.7% | 0.70% |
| conventional liquid for vaccine | mumps (HOSHINO strain) | 4.0 | 3.8% | ≦0.10% |

*: $\log_{10}TCID_{50}/ml$
☆: infective titer after heating/before heating × 100% = survival ratio of virus (Survival ratio of virus is calculated by replacing a $\log_{10}$-value of each infective titer to antilogarithmic number)

TABLE 2

Stability of lyophilized vaccine
Lyophilized live attenuated measles vaccine, strain AIK-C
Lyophilized live attenuated mumps vaccine, strain HOSHINO
Lyophilized live attenuated rubella vaccine, strain TAKAHASHI

| Vaccine | Lot# | Before heating | | 37° C. 1 week | | 45° C. 1 week | |
|---|---|---|---|---|---|---|---|
| | | No. tested | Titer* (M ± SD)** | No. tested | Decreased titer☆ (M ± SD) | No. tested | Decreased titer |
| Stabilizing agent of the present invention | | | | | | | |
| Measles | TV-2 | 5 | 4.3 ± 0.11 | 5 | 0.2 ± 0.22 | 5 | 1.1 ± 0.14 |
| | TV-3 | 5 | 4.3 ± 0.22 | 5 | 0.3 ± 0.20 | 5 | 1.7 ± 0.27 |
| | TV-4 | 5 | 4.6 ± 0.27 | 5 | 0.2 ± 0.14 | 5 | 1.8 ± 0.25 |
| | TV-5 | 5 | 4.4 ± 0.25 | 5 | 0.3 ± 0.30 | 5 | 1.7 ± 0.36 |
| | TV-6 | 5 | 4.3 ± 0.11 | 5 | 0.2 ± 0.11 | 5 | 1.7 ± 0.38 |
| Mumps | TV-1 | 5 | 5.2 ± 0.35 | 5 | 0.3 ± 0.31 | 5 | 1.6 ± 0.16 |
| | TV-2 | 5 | 5.1 ± 0.18 | 5 | 0.2 ± 0.18 | 5 | 1.6 ± 0.30 |
| | TV-3 | 5 | 5.2 ± 0.14 | 5 | 0.2 ± 0.27 | 5 | 1.4 ± 0.13 |
| | TV-4 | 5 | 5.0 ± 0.20 | 5 | 0.1 ± 0.16 | 5 | 1.3 ± 0.21 |
| Rubella | TV-1 | 5 | 4.5 ± 0.22 | 5 | 0.2 ± 0.11 | 5 | 0.9 ± 0.42 |
| | TV-2 | 5 | 4.6 ± 0.37 | 5 | 0.3 ± 0.11 | 5 | 0.8 ± 0.27 |
| | TV-3 | 5 | 4.5 ± 0.16 | 5 | 0.3 ± 0.17 | 5 | 0.8 ± 0.44 |
| | TV-4 | 5 | 4.5 ± 0.31 | 5 | 0.2 ± 0.18 | 5 | 0.9 ± 0.35 |
| Conventional stabilizing agent | | | | | | | |
| Measles | M10-1 | 5 | 4.5 ± 0.18 | 5 | 2.8 ± 0.21 | 5 | 4.4 ± 0.31 |
| | M10-27 | 5 | 4.1 ± 0.11 | 5 | 2.3 ± 0.25 | 5 | 4.0 ± 0.38 |
| | M11-7 | 5 | 4.4 ± 0.25 | 5 | 2.4 ± 0.33 | 5 | 4.3 ± 0.38 |
| | M11-11 | 5 | 4.6 ± 0.13 | 5 | 2.2 ± 0.21 | 5 | 4.1 ± 0.31 |
| Mumps | K01-12 | 5 | 5.1 ± 0.26 | 5 | 1.4 ± 0.29 | 5 | 3.7 ± 0.41 |
| | K01-18 | 5 | 4.3 ± 0.26 | 5 | 1.6 ± 0.21 | 5 | 3.6 ± 0.42 |
| Rubella | 823-11 | 5 | 4.4 ± 0.25 | 5 | 0.8 ± 0.16 | 5 | 1.5 ± 0.22 |
| | 823-15 | 5 | 4.5 ± 0.13 | 5 | 1.0 ± 0.23 | 5 | 1.8 ± 0.29 |

*: $\log_{10}TCID_{50}/ml$
**: mean ± S. D.
☆: (Titer before heating) − (titer after heating) = Decreased titer ($\log_{10}TCID_{50}/ml$)

We claim:
1. A stabilized live attenuated vaccine, which comprises a live attenuated plain vaccine consisting of measles, mumps or rubella virus grown in a medium-199 for cell culture, or a combined live attenuated vaccine thereof, in admixture with a stabilizing agent which is a combination consisting essentially of lactose 2.5–5 W/V%, saccharose 2.5–5 W/V%, D-sorbitol 1.8–2 W/V%, sodium glutamate about 0.1 W/V% and gelatin hydrolyzate, M.W. approx. 35,000, 2–3 W/V%.

2. A stabilized live attenuated vaccine according to claim 1 wherein the said vaccine is a lyophilized vaccine produced by lyophilizing a live attenuated plain vaccine consisting of measles, mumps or rubella virus grown in a medium-199 for cell culture, or a combined live attenuated vaccine thereof, in admixture with said stabilizing agent.

3. A process for preparing a live attenuated vaccine which comprises growing a seed virus in a medium-199 for cell culture to produce a live attenuated plain vaccine of measles, mumps or rubella, or a combined live attenuated vaccine thereof, adding said stabilizing agent thereto to prepare a stabilized live attenuated vaccine solution, and lyophilizing the said solution.

* * * * *